United States Patent
Spruiell (10) Patent No.: US 7,086,397 B2
(45) Date of Patent: Aug. 8, 2006

(54) PATIENT USABLE EMERGENCY MEDICAL KIT

(76) Inventor: Graham Lindley Spruiell, One Mendum St., Hingham, MA (US) 02131

(*) Notice: Subject to any disclaimer, the term of this patent is extended or adjusted under 35 U.S.C. 154(b) by 333 days.

(21) Appl. No.: 10/075,088

(22) Filed: Feb. 16, 2002

(65) Prior Publication Data

US 2003/0154981 A1    Aug. 21, 2003

(51) Int. Cl.
    *A61M 15/00* (2006.01)
(52) U.S. Cl. .......................... 128/200.24; 128/204.18; 128/205.22
(58) Field of Classification Search ........... 128/205.22, 128/206.28, 207.12, 200.24, 204.18, 205.24, 128/205.25
    See application file for complete search history.

(56) References Cited

U.S. PATENT DOCUMENTS

| | | | | | |
|---|---|---|---|---|---|
| 3,923,054 | A | * | 12/1975 | Bauer, Jr. .............. | 128/202.18 |
| 4,168,706 | A | * | 9/1979 | Fletcher et al. ........ | 128/204.16 |
| 4,169,550 | A | | 10/1979 | Williams | |
| 4,241,833 | A | | 12/1980 | Luebcke | |
| 4,257,415 | A | | 3/1981 | Rubin | |
| 4,365,628 | A | * | 12/1982 | Hodel .................. | 128/205.12 |
| 4,386,642 | A | | 6/1983 | Durbin | |
| 4,409,978 | A | * | 10/1983 | Bartos ................. | 128/205.12 |
| 4,438,764 | A | | 3/1984 | Eppolito | |
| 4,699,288 | A | * | 10/1987 | Mohan ................. | 220/590 |
| 4,844,307 | A | | 7/1989 | Rutledge | |
| 5,150,812 | A | * | 9/1992 | Adams ................. | 220/589 |
| 5,207,303 | A | | 5/1993 | Oswalt et al. | |
| 5,485,827 | A | * | 1/1996 | Zapol et al. .......... | 128/200.14 |
| 5,499,739 | A | * | 3/1996 | Greist et al. ......... | 220/589 |
| 5,561,134 | A | * | 10/1996 | Spada et al. ......... | 514/263.23 |
| 5,584,289 | A | * | 12/1996 | Wise .................... | 128/205.24 |
| 5,639,441 | A | * | 6/1997 | Sievers et al. ....... | 424/9.3 |
| 5,895,354 | A | * | 4/1999 | Simmons ............. | 600/301 |
| 5,904,938 | A | * | 5/1999 | Zapol et al. .......... | 424/718 |
| 6,047,860 | A | | 4/2000 | Sanders | |
| 6,063,407 | A | * | 5/2000 | Zapol et al. .......... | 424/718 |
| 6,141,589 | A | * | 10/2000 | Duhaylongsod ..... | 607/10 |
| 6,190,481 | B1 | * | 2/2001 | Iida et al. ............ | 156/175 |
| 6,279,580 | B1 | | 8/2001 | Perez et al. | |
| 6,292,687 | B1 | * | 9/2001 | Lowell et al. ........ | 600/515 |

(Continued)

OTHER PUBLICATIONS

General Pharmacologic Treatment of Acute Myocardia Infarction Anne Warden Shannon MD Richard Harrigan MD.

*Primary Examiner*—Glenn K. Dawson
*Assistant Examiner*—Michael G. Mendoza
(74) *Attorney, Agent, or Firm*—Edward L. Kelley; DBA Invention Management Associates (57) ABSTRACT

The invention provides an emergency medical kit for use immediately upon the onset of symptoms of an attack of a vascular disease such as a heart attack or a stroke. The emergency medical kit at least includes breathable oxygen in a light weight container and may include medications for preventing thrombosis, inducing arteriolar relaxation or assisting in diminishing oxygen demand by the victim. The kit including oxygen and medication dosage may be prescribed by a physician to a person with a known susceptibility to a serious unexpected attack of a vascular disease. The treatment provided by the contents of the kit is specifically intended to save the life of an attack victim and or to reduce permanent tissue damage in the victim during the time interval between the onset of the attack and the arrival of a professional medical service provider. The kit is lightweight and readily carried by the user or stored in a location for easy access.

7 Claims, 3 Drawing Sheets

U.S. PATENT DOCUMENTS

| | | |
|---|---|---|
| 6,327,497 B1 | 12/2001 | Kirchgeorg et al. |
| 6,369,064 B1 * | 4/2002 | Brown et al. ............ 514/261.1 |
| 6,462,050 B1 * | 10/2002 | Isaacs et al. ........... 514/255.05 |
| 6,552,014 B1 * | 4/2003 | Serebruany et al. ... 514/214.02 |
| 6,578,571 B1 * | 6/2003 | Watt ...................... 128/200.14 |
| 6,581,599 B1 * | 6/2003 | Stenzler ................. 128/204.23 |
| 6,656,452 B1 * | 12/2003 | Zapol et al. ................... 424/45 |
| 6,811,768 B1 * | 11/2004 | Zapol et al. ................... 424/45 |

* cited by examiner

PATIENT USABLE EMERGENCY MEDICAL KIT

BACKGROUND OF THE INVENTION

1. Field of the Invention

The present invention generally relates to an emergency medical kit for self-administration or assisted administration of breathable oxygen. A medication is also provided for relief of symptoms of a serious illness. In particular, the emergency medical kit is provided to a person that is prone to or at risk of the serious illness and the kit is intended to be used as soon as symptoms of the serious illness appear or are suspected and up until a the person is treated by a trained medical professional.

2. Description of Related Art

It is a particular problem that an unexpected attack of serious illnesses may cause death or serious and irreversible injury. This is particularly a problem during the first moments after the onset of the unexpected attack or symptoms of the illness and up until a time when a trained medical practitioner can medically treat the person. It is well known that prompt medical treatment can greatly reduce the risk of death or of serious permanent injury from an attack of a serious illness. The reason that early treatment of the victim is often successful is that a trained medical practitioner, e.g. in an emergency response team (ERT) or in a hospital, has access to the appropriate equipment and medications that may be needed to save the life of the person or to prevent extensive and irreversible damage to the victim. In heart attack and stroke victims, the main cause of death and or serious permanent injury is mainly due to inadequate oxygenation to affected areas, which may result from reduced blood flow. If prolonged, inadequate oxygenation will lead to death or permanent tissue damage. It is well known that inadequate oxygenation can be relieved by administration of breathable oxygen. Oxygen breathed by a person in trauma increases oxygen saturation in the blood, which decreases the possibility of tissue damage from infarction during an ischemic event caused by an obstruction of blood circulation such as may occur in heart attack or stroke or other arterial illness or condition. Moreover, medications are available that may further benefit a seriously ill patient in crisis during the first moments after the onset of symptoms. However, it is typical that neither oxygen nor a proper medication is readily available to a victim until after trained medical help arrives or until after the victim reaches a hospital. By this time, it may be too late.

United States medical figures show that of the 1.1 million people who suffer heart attacks annually, 40% will die. It is known that some of the fatal heart attack victims may have been saved had they received medical treatment with the first hour after the onset of symptoms. Unfortunately, only one in five Americans who have a heart attack get to a hospital within one hour. The situation is similar with stroke victims. Of the 600,000 Americans that experience a stroke each year, 160,000 of them die and 67% of the survivors suffer from disabilities. Moreover, the risk of stroke increases dramatically as a person ages past 55 years old and is especially increased in elderly women. In both heart attack and stroke, a lack of oxygen results in permanent destruction of tissue or infarction. It is well known that a supply of supplemental oxygen, such as breathable oxygen, can alleviate some of the damage resulting from infarction and that this is often the first medical treatment provided to an apparent heart attack or stroke victim by a medically trained person. It is also well known that various medications including non-prescription medications such as aspirin and nitroglycerin can be beneficial if administered in the first hour after a heart attack or stroke.

Recently is has become more recognized that early medical attention is critical in reducing permanent damage to tissue from a heart attack or a stroke. In addition, there is a recognized need to better educate both the medical community and the general public about the benefits of; early recognition of the symptoms of a heart attack and especially a stroke; and, the early treatment of a heart attack or a stroke in the minutes following the on set of the symptoms. This is especially true for persons that may be prone to, or have a high risk of, suffering a heart attack or a stroke.

Unfortunately, education may not be good enough because the time that it takes for an emergency medical technician, (EMT) to arrive, recognize and treat the symptoms of a heart attack or a stroke victim may be too long. Depending on a victims location, the response period may be between about 15–60 minutes, in an urban location, 1–2 hours in a rural location or more than 2 hours if the victim is aboard an aircraft or sailing vessel. Meanwhile, even if the victim or a bystander recognizes the symptoms there is usually no readily available oxygen supply or medication source that could be used to prevent death or permanent tissue damage during the first hour, as may be essential.

One solution to the problem has been to place portable emergency medical devices such as an automatic external defibrillator, (AED), including electrode paddles and a DC battery or other power supply in public areas such as in commercial buildings, airliners, ships and installed onto emergency response vehicles. These devices may be used to immediately treat a heart attack victim by defibrillating the heart muscle. Such a device may save the victims life, in the first moments after a heart attack. In a recent U.S. Pat. No. 6,327,497 by Kirchgeorge et al., and assigned to Life Corporation, an emergency medical kit is taught that includes an AED and a breathable oxygen source housed in a portable unitary casing. The '479 kit also includes an oximeter for measuring oxygenation, a pulse meter, a liquid crystal display (LCD) screen, for providing measurement monitoring, and text display, a voice prompt system and a speaker for providing audio feedback. Although the '497 kit provides an oxygen supply, the inclusion of the AED clearly shows that the device should only be used by a trained medical technician. In addition, the '497 kit does not include any medications.

In general, an AED is provided as an emergency response tool that can save the life of a heart attack victim. However, a portable AED requires a portable power supply and it's use and operations are not obvious to an untrained person. In fact, use of an AED is not recommended for an untrained person. It is another shortcoming of an AED that treatment cannot be self-administered. The portable power and electronics of the AED are expensive to manufacture and difficult to use. Accordingly, an emergency medical kit that includes an AED tends to be expensive and therefore not readily available for home use or generally available to a person prone to or at risk of a heart attack or a stroke. Moreover, any kit containing an AED is complex and not likely to be usable by the victim.

Accordingly, there is a need in the art to provide a simple low cost and portable emergency medical kit that could save the live of a heart attack or a stroke victim during the first hour after the onset of symptoms. Ideally, the medical kit will be readily affordable for a person prone to or at risk of having a heart attack or a stroke or another serious illness for which early medical treatment could save the life of, or prevent permanent damage to, the victim. Moreover, the medical kit and the treatment should be self-administrable if the victim is alone. Furthermore, the emergency medical kit should be able to be stored and used in the home, an automobile, or any other vehicle and should allow the patient to carry the kit wherever the patient may decide to travel.

Several examples exist for a simple and portable emergency medical kit and carrying case for providing breathable oxygen and some of these are taught in U.S. Pat. Nos. 5,207,303, 4,197,842 and 4,438,764. However, these references appear to be directed only to use by a trained medical professional and none of these references includes the use or storage of any medications to be administered to or self-administered by a person displaying symptoms of a serious illness such as a heart attack or a stroke.

BRIEF SUMMARY OF THE INVENTION

The present invention overcomes the problems cited in the prior art by providing a patient usable emergency medical kit that includes a breathable oxygen supply and a medication that may benefit a person displaying symptoms of a heart attack, a stroke or another medical condition that may cause, infarction or otherwise reduce oxygenation in the victim. The patient usable emergency medical kit is compact and lightweight for easy portability. Moreover, the medical kit requires no power supplies or electronics to provide a potentially life saving treatment. The kit is self-explaining and usually does not require special training to operate or administer the required treatment to a victim of a serious illness and if the victim is able, the treatment provided may be self-administered. The emergency medical kit of the present invention is particularly beneficial for a person that may be prone to or at risk of suffering from a particular medical condition that may result in infarction, from an ischemic event, or may suffer any risk from otherwise reduced oxygenation. A physician will prescribe the emergency medical kit to a patient that is prone to or at risk of suffering a particular serious illness. The treatment provided by the contents of the kit should at least include the administration of breathable oxygen. The treatment may also include the administration of a medication for assisting in saving the life of or reducing permanent tissue damage in the victim.

The emergency medical kit may be stored and carried in a portable bag or container that may include handles and or straps for each of transporting the medical kit and which may also serve to help support the breathable oxygen supply during it's use by attaching the bag or container to the victim.

In particular, the invention is an emergency medical kit that includes a breathable oxygen delivery system and may include another medication. The breathable oxygen delivery system includes a portable oxygen tank for storing oxygen under high pressure and the portable oxygen tank may be formed using a composite material over wrapped onto a gas impermeable inner vessel. In that case the portable oxygen tank may weigh as little as 1½ pounds when empty and as little as 2⅛ full. The emergency medical kit may also include a wireless communication device or a loud noise-making device or both to contact someone in the event of an emergency. A physician will prescribe the oxygen and any other medication for a particular user if the user has a known susceptibility to heart attack, stroke or other conditions that may benefit from oxygenation and a medication.

The medications provided may include any one of anti-coagulants such as acetylsalicyclic acid, clopidogrel, heparin and glycoprotein IIb/III/b inhibitors, nitrates such as nitroglycerin, cardioprotective agents such as beta blocker, antiarrhythmics such as magnesium and vasoactive agents such as ACE inhibitors.

In particular any medication for assisting in preventing thrombosis, assisting in inducing arteriolar relaxation, assisting in establishing cardiac rhythm or assisting in diminishing oxygen demand may be included in the medical kit and may be beneficial in the treatment of heart attack, stroke and or any other arterial conditions that may cause infarction.

BRIEF DESCRIPTION OF THE DRAWINGS

The features of the present invention will best be understood from a detailed description of the invention and a preferred embodiment thereof selected for the purposes of illustration and shown in the accompanying drawing in which.

DETAILED DESCRIPTION OF THE INVENTION

Reference will now be made in detail to the preferred embodiments of the present invention, examples of which are illustrated in the accompanying drawings.

Figure 1:
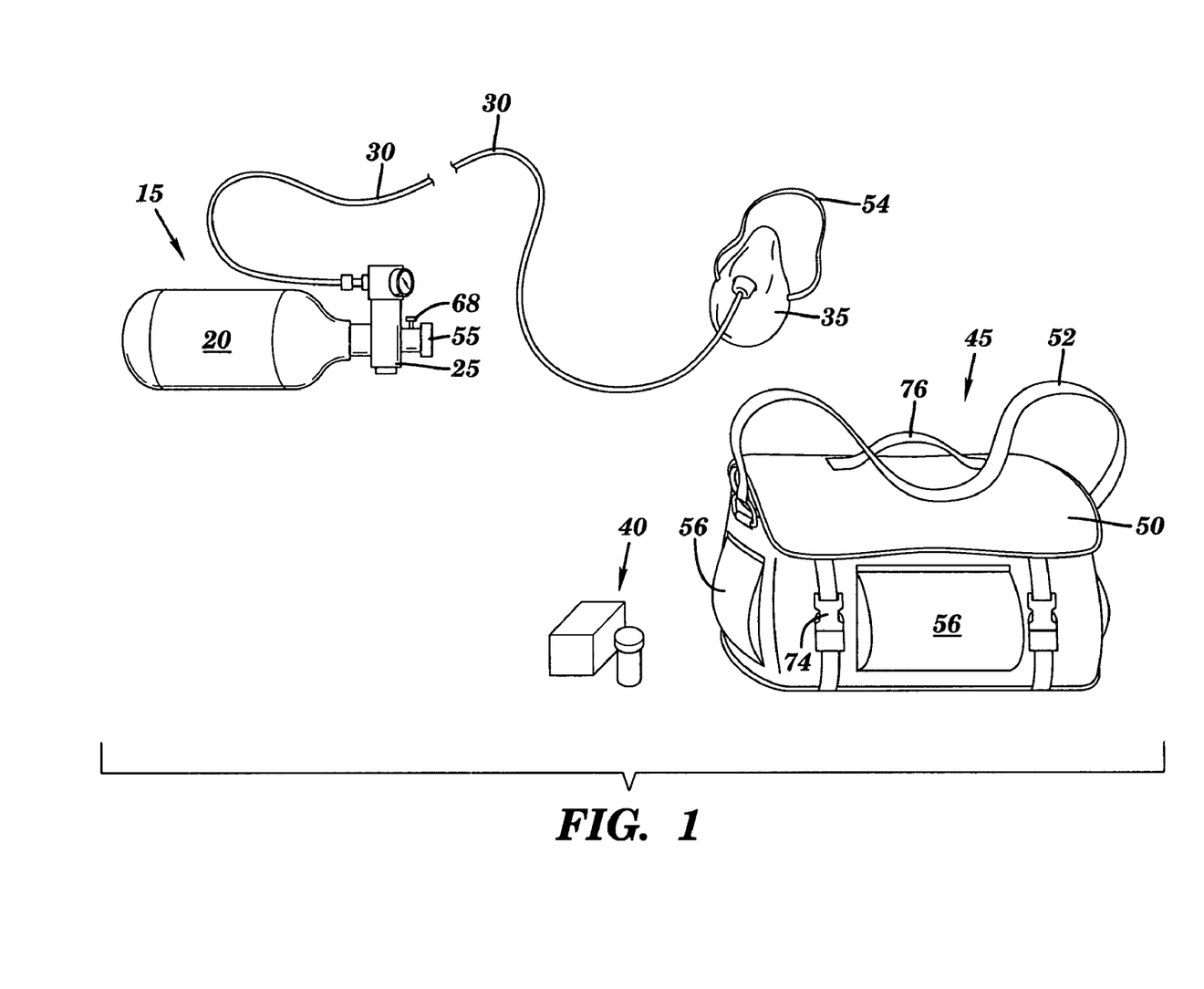
FIG. 1 illustrates a medical kit according to the present invention.

Referring now specifically to FIG. 1, the first embodiment illustrates the emergency medical kit 10. The kit includes a breathable oxygen delivery system 15 comprising a portable oxygen tank 20, containing an oxygen supply stored at a high pressure, a regulating oxygen delivery valve 25, for regulating the pressure of oxygen as it exits the oxygen tank, a hollow delivery tube 30 and a facemask 35 for delivering breathable oxygen to a patient. The kit 10 further includes one or more containers of medication 40 and a portable bag or container 45 for storing the breathable oxygen delivery system 15 and the medication 40 therein.

Figure 2:
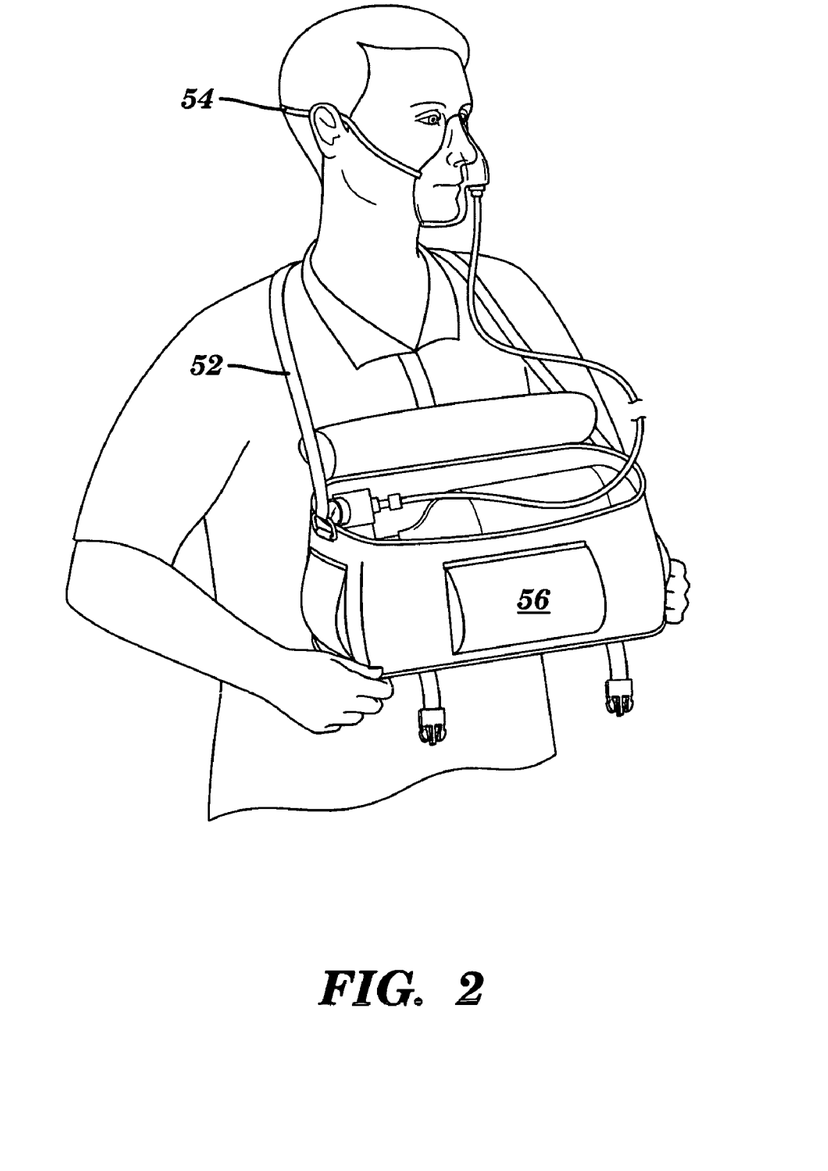
FIG. 2 illustrates a patient user using the medical kit according to the present invention.

As illustrated in FIG. 2 a patient or user is shown using the emergency medical kit 10. According to the invention, the breathable oxygen delivery system 15 is stored in the portable bag or container 45, which includes a cover 50 that may be either opened or closed during use. The bag 45 further includes a strap 52 which is sufficiently long for hanging the bag 45 over the neck of the user, during use, and which may also serve as a shoulder strap for carrying or supporting the bag 45, while in use or otherwise. As shown in FIG. 2 the user places the facemask over the nose and mouth and breaths normally. The facemask may also be configured for nose only or mouth only installation. The mask may also include vents, (not shown), for easy discharge of the exhaled breath of the patient. A head strap 54 or other securing device is provided to secure the facemask in place during use. Oxygen is delivered to the facemask by the pressure tank 20 via the regulator valve 25 and the tube 30. A handle 55 is provided on the regulator valve 25 for manually turning a valve stem within the regulator valve for sealing the regulator value, thereby blocking the flow of oxygen from the tank 20 during periods of none use. The valve may be manually opened to start the flow of oxygen to the mask 35.

The containers of medications 40 may also be stored in the bag 45, or attached to the oxygen delivery system 15, or otherwise stored in the kit 10. The bag 45 may also include one or more external and internal easy open pockets 56 for storing the medication containers 40. In addition, the pockets 56, the medication containers 40, or both, may be clearly labeled with a name of the medication or with a universal medical symbol such as a graphic character representative of a medication to alert the user or someone assisting the user to the presence of the medication. In any case, the containers of medication 40 should be clearly marked and readily available in an emergency. Moreover, the medication and the method of delivering the medication should be simple enough for an untrained person to administer in an emergency. Preferably the medication may be a liquid or an easy swallowed pill or capsule that is orally administered by the user or by someone assisting the user. Of course other means such as a topical or skin patch application, a needle or an air injection are also possible. In a preferred embodiment, the containers of medication 40 are packaged in manner suitable for preventing exposure to damaging agents such as water, sunlight, or other agents that may destroy the medications or render them less potent. Accordingly the containers of medication 40 may be wrapped in moisture resistant or waterproof material such as a shrink-wrap plastic or resealing clear plastic bag or in a water tight container.

Figure 3:
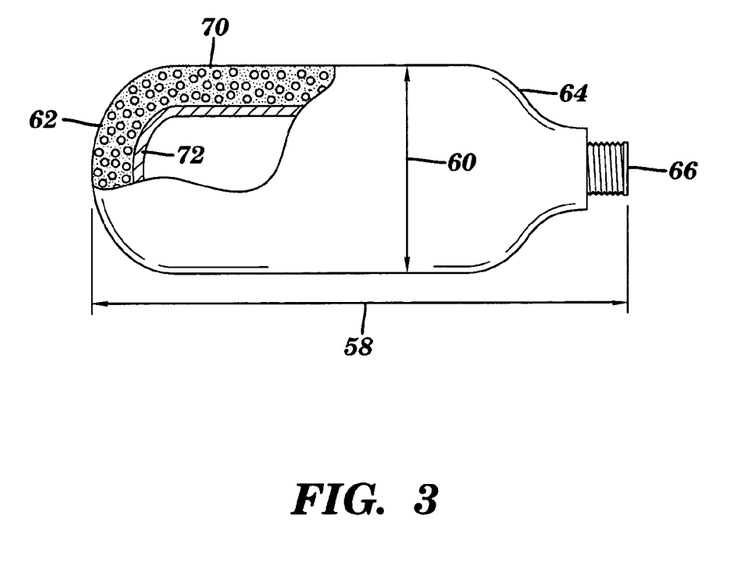
FIG. 3 illustrates details of a pressure vessel according to the present invention.

In accordance with a preferred embodiment of the invention, the oxygen tank 20 comprises a carbon/glass/epoxy composite material 70 such as a filament over-wrapped onto a gas impermeable inner vessel 72, shown in partial section in FIG. 3. One such vessel is taught in U.S. Pat. No. 6,190,481, assigned to Toray Industries in Japan, which is incorporated herein by reference. An envelope wound pressure vessel particularly suitable for the preferred embodiment of the present invention is made and distributed by Structural Composite Industries, (SCI) of Azusa, Calif. The pressure vessel 20 may comprise a gas impermeable aluminum liner 70, such as a 6061-T6 alloy, an epoxy resin over wrap material 72 and a carbon/glass reinforcing material. In one example, the tank 20 may have an overall length 58 of about 7.5 inches and an outer diameter 60, of about 4.5 inches. In this embodiment, spherically rounded end portions 62 and 64 are provided. The tank internal volume measures about 67 cubic inches. The tank 20 may further includes a mail threaded boss portion 66 for attaching a regulator valve 25 thereto.

In accordance with the a preferred embodiment of the present invention, the tank 20 may have a service pressure of up to about 3000 pounds per square inch, (PSI) and a test pressure of up to about 5000 PSI. Of course higher and lower pressures may also be used. In the present example, the tank 20 has an empty weight of 1.5 pounds and a filled weight of 2.12 pounds, not including the regulator valve 25. The tank 20 is operable over a temperature range of about −60 degrees F. to +140 degrees F. and has a service life of up to about 15 years. Finally the tank 20 should be approvable by the Food and Drug Administration, FDA for the storage of breathable oxygen and the tank may be refillable after use. Of course other tanks designs are usable without deviating from the scope of the present invention, including an all-metal tank, an all-plastic tank or combinations of metals, plastics or various composite materials. However, it is particularly desirable for portability and ease of use that the tank 20 when full weight less than about 5 pounds so that the entire emergency medical kit weight is light enough to provide easy portability. Such features have heretofore not been readily available for use as an FDA approved oxygen storage vessel for medical application of breathable oxygen.

The oxygen regulator valve 25 is attached to the tank 20 and receives high-pressure oxygen from the tank 20 at an inlet pressure in a range of about 250–3000 PSI and delivers low-pressure oxygen to the flow tube 30 at an outlet pressure in a range of about 20–50 PSI. Of course the valve may also receive and deliver a wider range of pressures, for example, regulator valves may be provided for operating with an inlet pressure of between 100–4000 PSI and an outlet pressure ranging from about 1 PSI up to about 100 PSI. The valve 25 may also include a handle 55 for opening and closing the valve 25 and for adjusting the flow rate to the tube 30. In one embodiment, the valve handle 55 may have a plurality of positions each associated with a different flow rate for passing oxygen to the tube 30. The flow rates may be adjustable in a range of about 20 cubic centimeters per min up to 60 liters per minute. In most applications for providing breathable oxygen to a patient, a recommended flow rate will be in the range of about 3 to 8 liters per minute, (LPM) and may vary according to the needs of the particular patient. In order to provide an appropriate flow rate to a patient, the regulator valve 25 may include a stop device such as a movable pin 68 for stopping the handle at a desired orientation when the valve is turned to a position that delivers the appropriate rate. Otherwise the valve handle 55 or the regulator valve 25 may be marked with flow rate indicating marks. Alternately, a flow meter may be provided for measuring a flow rate to the patient such that the flow rate may be adjusted by turning the valve 55. In the preferred embodiment described herein, a flow rate is preferable set at 6 LPM. In the simplest embodiment, a flow rate of 6 LPM would be achieved by turning the handle 55 to the full on position. Using the tank 20 described above which has an initial operating pressure of 3000 PSI and an internal volume of 67 cubic inches, the tank 20 will provide oxygen to a patient for about 39 minutes. Of course, if longer times are desired, the tank 20 may include a larger volume vessel or store the oxygen at an increased pressure.

A preferred embodiment of the container for storing the breathable oxygen supply 15 and medications 40 comprises a flexible and soft bag 45 shown in FIGS. 1 & 2. The bag 45 may comprise nylon, canvas or another conventional flexible bag material. The bag 45 may include a cover 50, which is held closed by clamps 74, so that the materials of the kit may be held inside the bag. As stated above the bag 45 may include one or more internal or external pockets 56 for securing medications 40 therein or for storing other personal affects of the patient including other medications that may be taken in non-emergency situations. The pockets 56 may be sealed by a zipper, a clamp, VELCRO or by any other convenient sealing device. The bag 45 is preferably weather and tear resistant and may provide a cushioning or padding for protecting the contents thereof in the event the bag is dropped. The bag 45 may also include one or more handles 76 and or straps 52.

Numerous medications are known to be beneficial to a victim of a heart attack or a stroke. It has been shown that effective treatment of acute myocardial infarction, (heart attack), may include oxygen, agents affecting thrombus formation, nitrates, beta blockers, antiarrhythmics and morphine. (See GENERAL PHARMACOLOGIC TREATMENT OF ACUTE MYOCARDIAL INFRARCTION by, Anne Warden Shannon MD and Richard A, Harrigan MD, Temple University Hospital) Where it is known that a person is at risk of a heart attack, a medical kit of the present invention is prescribed by a physician and the medical kit would at least include a breathable oxygen supply and one or more of the other treatments. At the present time, oxygen and most medications, must be prescribed by a physician in the United States. However, it is possible that the kit of the present invention may become available over the counter especially outside the United States and may be used with prescribed or over the counter medications.

The administration of breathable oxygen, which is the first and foremost recommended treatment for a heart attack and for a stroke, is here addressed by the use of the breathable oxygen supply described above. In this case oxygen is prescribed by a physician like any other medication and has the effect of increasing oxygen saturation in the blood when the person is in trauma. Oxygen may be prescribed to treat any attack that may result in reduced oxygenation in the blood caused by thrombosis ischemic events or any reduced blood flow. The immediate administration of oxygen reduces the risk of infarction and may prevent death.

The second treatment includes agents affecting thrombus formation or blood clotting. Antithrombotics are known to be beneficial in both heart attack and stroke and in a variety of other arterial conditions that may cause infarction and or reduced oxygenation to the affected area. Agents affecting thrombus formation may include anticoagulants, or anti-platelets, which inhibit platelet aggregation.

In particular, oral antiplatelet agents have been established as essential in the management of a heart attack victim and these specifically include acetalylacylic acid or aspirin and clopidogrel. Aspirin irreversibly inhibits platelet cyclo-oxygenase, which subsequently prevents the formation of thromboxane $A_2$. This, in turn, impairs platelet aggregation. Clopidogrel inhibits adenosine diphosphate (ADP)-mediated platelet aggregation. A new aspirin-dipyridamole combination agent that has received FDA approval for stroke prevention is also an excellent candidate for use in either stroke or heart attack treatment during the first hours. One study has shown that aspirin can reduce the risk of death by up to 23% if administered when a heart attack is suspected and for 30 days thereafter. This represents a potential for saving 10,000 lives per year in the United States alone. Clopidogrel has been found to be effective in reducing the combined risk of ischemic stroke, heart attack, or death from vascular disease and is therefore a medication candidate for emergency treatment of stroke, heart attack or vascular disease during the first hours. However, because aspirin and clopidogrel affect platelet function by different mechanisms, they may be usable in combination to achieve greater benefit. Accordingly, aspirin and clopidogrel each make an excellent candidate for inclusion in the medical kit of the present invention because each medication may provide a substantially immediate benefit to a victim of stroke, heart attack or vascular disease.

Other medications that may be used also include cardioprotetctive agents, e.g., beta-adrenergic antagonists (Beta Blockers), antiarrythmics, such as magnesium, and other vasoactive agents such as angiotensin converting enzyme (ACE) inhibitors. Beta Blockers may diminish myocardial oxygen demand by reducing heart rate, blood pressure and contractility. Beta Blockers have also been shown to decrease cardiac ischemia-reducing myocardial wall stress and infarct size. They have also been shown to decrease ventricular arrhythmias (including ventricular fibrillation) and to improve left ventricular function. In short, Beta Blockers have a well-established, evidence-based role in both emergency and follow-up care of heart attack victims as a means to short-term mortality reduction.

Magnesium has several potential mechanisms of action that can benefit heart attack victims. It can decrease the rate of arrhythmias by enhancing membrane stability and reducing the effects of free radicals. It also causes coronary vasodilatation, afterload reduction, calcium antagonism, and has antiplatelet activity. Angiotensin-converting enzyme inhibitors, (ACE) inhibitors, can be helpful early in the treatment of a heart attack and ideally after thrombolytic therapy has been given and the blood pressure is known to be stable. Benefits of ACE inhibitors include suppression of the sympathetic and renin-angiotensin systems, and enhanced collateral coronary blood flow in addition to ventricular remodeling. Patients with conditions such as anterior wall myocardial infarction, previous infarction, congestive heart failure, or tachycardia seem to derive greater benefit from treatment with ACE inhibitors. Some examples of Beta Blockers and Calcium channel blocking drugs are listed below in TABLE 1.

TABLE 1

| Drug | Usual Dose | Side Effect | Contadictions |
|---|---|---|---|
| BETA BLOCKERS | | | |
| Propranolol | 20–80 mg qid | Depression, constipation, impotence, bronchospasm, heart failure, bradycardia | Asthma, AV conduction block, heart failure |
| Metoprolol | 25–200 mg bid | As above | As above |
| Atenolol | 50–150 mg once daily | As above | As above |
| CALCIUM CHANNEL BLOCKING DRUGS | | | |
| Nifedipine XL | 30–90 mg daily | Hypotension, flushing, edema, worsening angina | Hypotension, intolerance of side effects |
| Diltiazem SR | 60–120 mg bid | Constipation, AV conduction block, worsening heart failure | AV conduction block, impaired LV function, bradycardia |
| Verapamil SR | 180–240 mg daily | Constipation, AV conduction block, worsening heart failure | AV conduction delay, impaired LV function, bradycardia |
| Amlodipine | 5–10 mg daily | Edema | Intolerance of side effects |

Nitrates have the effect of relaxing vascular smooth muscles, which helps to dilate both arterial and venous beds, although venous effects predominate. Nitroglycerin is a commonly recommended nitrate that provides dilation of post capillary vessels, including large veins, promotes peripheral pooling of blood, decreases venous return to the heart, and reduces left ventricular end-diastolic pressure (preload). Nitroglycerin also produces arteriolar relaxation, thereby reducing peripheral vascular resistance and arterial pressure (afterload), and dilates large epicardial coronary arteries. The use of nitrates upon the onset of heart attack symptoms has long been recommended. Some examples of nitrates dosage, side effects and contradictions are provided in TABLE 2 below.

TABLE 2

| Drug | Usual Dose | Side Effects | Contraindications |
|---|---|---|---|
| NITRATES | | | |
| Sublingual NTG Isosorbide dinitrate SR | 0.3–0.6 mg | Flushing, headache | Intolerance of side effects |
| Oral Sublingual Transdermal NTG patch Isosorbide-5-monitrate | 10–60 mg q8 h 2.5–10 mg q4–6 h 0.4–1.2 mg/h for 12–14 h | Flushing, headache, tolerance after 24 h Flushing, headache, tolerance after 24 h | As above, worsening ischemia on withdrawal As above, worsening ischemia on withdrawal |
| Oral Oral SR | 20–30 mg bid 60–240 mg once daily | Flushing, headache, tolerance after 24 h | As above, worsening ischemia on withdrawal |

According to the present invention, a person that has had a previous heart attack, has arterial or venous disease or is at high risk of either would carry a medical kit that includes breathable oxygen and a medication that may reduce the tendency for blood clotting, reduce the need for oxygen, slow the heart rate, maintain cardiac rhythm relax the arteries and veins or protect the brain from secondary injury due to lack of oxygenation caused by stroke. The medication type and dosage will be predetermined by a physician in advance and packed in the kit of the present invention. The kit could be provided for everyday availability or to a person or could be provided to a person temporarily if the person will be far from medical attention, e.g. in a remote area or on a sailing vessel. The selection of the medication will be determinable by the personal physician of the person. Thus according to the present invention, the emergency kit may include anyone of the above listed agents that affect thrombus or blood clot formation including acetylsalicyclic acid, aspirin-dipyridamole, clopidogrel, heparins and glycoprotein IIb/IIIa inhibitors. The kit might also include various so-called cardioprotetctive agents such as beta-adrenergic antagonists (Beta Blockers), antiarrhymics such as magnesium, angiotensin converting enzyme (ACE) inhibitors and other agents affective in treating cardiac trauma. In particular, the present invention may comprise breathable oxygen in combination with any medications which may be provided either individually or in combination as prescribed or otherwise recommended by a physician or health professional to prevent death, reduce permanent damage or alleviate pain in the event of a heart attack, stroke, arterial trauma or any other attack of an illness that may be alleviated by breathable oxygen and medication in combination. In addition, the patient to whom the medical kit is provided should be informed of what symptoms or indications to look for and be instructed in the use of both the oxygen and the medication in the case of an emergency. The kit is portable so the patient may carry it when traveling or readily available in the home or vehicle of the patient should an attack occur. In addition to the above, the emergency medical kit of the present invention may also include a wireless emergency communication device such as cell phone or emergency call transponder device to alert a local emergency medical team or to directly alert the patient's physician in the event of an emergency. The kit may also beneficially include a loud noise-making device such as a whistle or air horn should the victim need to draw attention to him or her in the event of an emergency. However, it is pointed out that according to the present invention, no electrical device is required for providing treatment.

It will also be recognized by those skilled in the art that, while the invention has been described above in terms of preferred embodiments, it is not limited thereto. Various features and aspects of the above-described invention may be used individually or jointly. Further, although the invention has been described in the context of its implementation in a particular environment, and for particular applications, e.g. in a portable emergency medical kit, those skilled in the art will recognize that its usefulness is not limited thereto and that the present invention can be beneficially utilized in any number of environments and implementations. Accordingly, the claims set forth below should be construed in view of the full breadth and spirit of the invention as disclosed herein.

The invention claimed is:

1. A method for increasing a patient's chance to survive a sudden ischemic event without suffering permanent tissue damage comprising the steps of:
   establishing that the patient has a high risk of suffering the sudden ischemic event;
   identifying one or more medications and dosage amounts that would be suitable for the patient to take in combination with breathable oxygen to increase the patient's chance to survive the sudden ischemic event without suffering permanent tissue damage in the event that the sudden ischemic event occurs;
   prescribing the medications in a form suitable for self-administration during the sudden ischemic event;
   providing the patient with a portable emergency medical kit comprising the prescribed medications in the dosage amount identified and in the form suitable for self administration and a portable oxygen tank (20), pressure regulating valve (25), hollow delivery tube (30) and facemask (35) configured to deliver breathable oxygen to the patient at an appropriate pressure and flow rate during the sudden ischemic event;
   informing the patient of what symptoms to look for and instructing the patient in the use of the breathable oxygen and the medications in the event that the sudden ischemic event occurs; and, instructing the patient to keep the emergency medical kit readily available for use.

2. The method of claim 1 wherein the step of identifying one or more medications and dosage amounts further comprises the step of:

identifying one of magnesium, nitroglycerin, a beta-adrenergic antagonist (Beta-Blocker), a calcium channel blocker and an angiotensin-converting enzyme (ACE) inhibitor.

3. A method for increasing a patient's chance to survive a sudden ischemic event without suffering permanent tissue damage comprising the steps of:

prescribing one of acetylsalicylic acid, dipyridamole, clopidogrel, heparin and a glycoprotein IIb/IIIa inhibitor in a dosage amount suitable for preventing thrombosis and in a form suitable for self administration;

prescribing breathable oxygen to be administered to the patient as soon as symptoms of the sudden ischemic event occur;

providing the patient with an emergency medical kit containing the prescribed medications and a portable oxygen tank (20), pressure regulating valve (25), hollow delivery tube (30) and facemask (35) configured to deliver breathable oxygen to the patient at an appropriate pressure and flow rate during the sudden ischemic event;

informing the patient of what symptoms to look for and instructing the patient in the use of the breathable oxygen and the medications in the event that the sudden ischemic event occurs; and, instructing the patient to keep the emergency medical kit readily available for use.

4. The method of claim 1 wherein the step of identifying one or more medications and dosage amounts further comprises the step of identifying a nitrite selected from the group of, nitroglycerin, isosorbide dinitrate, and isosorbide monitrate.

5. The method of claim 1 wherein the step of identifying one or more medications and dosage amounts further comprises the step of identifying magnesium.

6. The method of claim 1 wherein the step of identifying one or more medications and dosage amounts further comprises the step of identifying aspirin and clopidogrel.

7. The method of claim 1 wherein the step of identifying one or more medications and dosage amounts further comprises the step of identifying aspirin-dipyridamole.

\* \* \* \* \*